US008282797B2

(12) United States Patent
Hyland et al.

(10) Patent No.: US 8,282,797 B2
(45) Date of Patent: Oct. 9, 2012

(54) ELECTRODE PRECONDITIONING

(75) Inventors: Mark Hyland, Yarnton (GB); Alan Maxwell Bond, Yarnton (GB)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 650 days.

(21) Appl. No.: 11/630,494

(22) PCT Filed: Jun. 29, 2005

(86) PCT No.: PCT/GB2005/002551
§ 371 (c)(1),
(2), (4) Date: Dec. 21, 2006

(87) PCT Pub. No.: WO2006/000827
PCT Pub. Date: Jan. 5, 2006

(65) Prior Publication Data
US 2009/0159464 A1   Jun. 25, 2009

(30) Foreign Application Priority Data
Jun. 29, 2004   (GB) .................................. 0414548.8

(51) Int. Cl.
*G01N 27/403* (2006.01)
(52) U.S. Cl. .................... 204/406; 204/434; 205/775
(58) Field of Classification Search .................. 204/402, 204/434, 406; 205/775, 789.5
See application file for complete search history.

(56) References Cited

U.S. PATENT DOCUMENTS

| 4,496,454 | A | * | 1/1985 | Berger ........................ 204/402 |
| 5,185,256 | A |   | 2/1993 | Nankai et al. |
| 5,324,400 | A |   | 6/1994 | Eliash et al. |
| 6,174,420 | B1 |  | 1/2001 | Hodges et al. |
| 2003/0132125 | A1 | * | 7/2003 | Wayment et al. ............. 205/792 |
| 2005/0067304 | A1 | * | 3/2005 | King et al. ..................... 205/794 |
| 2006/0008581 | A1 |   | 1/2006 | Hyland |

FOREIGN PATENT DOCUMENTS

| EP | 0 396 788 | * 11/1990 |
| WO | WO 03/012417 | 2/2003 |
| WO | WO 03/046538 | 6/2003 |
| WO | WO 03/056319 | 7/2003 |
| WO | WO 2005/121762 | 12/2005 |

(Continued)

OTHER PUBLICATIONS

Freiberg et al, Plating Surf. Fin. 70(10), pp. 55-60 (1983).*

(Continued)

*Primary Examiner* — Kaj K Olsen
(74) *Attorney, Agent, or Firm* — Quarles & Brady LLP; George E. Haas

(57) ABSTRACT

An electrochemical sensing method that includes (a) providing an electrochemical cell having a working electrode and a pseudo reference electrode; (b) providing a sample comprising a metal, the sample being in contact with the working electrode and the metal being capable of being oxidized or reduced at the working electrode when the metal is bound to the working electrode; (c) preconditioning the working electrode by (i) applying a time varying preconditioning potential between the working and pseudo reference electrodes; and/or (ii) baking the working electrode; and/or (iii) air-ageing the working electrode; and (d) applying a measuring potential between the working and pseudo reference electrodes and, during application of said measuring potential, measuring the current generated by oxidation/reduction of the metal at the working electrode.

6 Claims, 5 Drawing Sheets

FOREIGN PATENT DOCUMENTS

| | | |
|---|---|---|
| WO | WO 2006/000823 | 1/2006 |
| WO | WO 2006/000828 | 1/2006 |
| WO | WO 2006/000829 | 1/2006 |

OTHER PUBLICATIONS

Princeton Applied Research 363 Potentiostat Specifications. Date unknown.*

Bard and Faulkner, Electrochemical Methods: Fundamentals and Applications, 2001, pp. 652-654.*

L.I. Netchiporouk, et al., Properties of Carbon Fibre Microelectrodes as a Basis for Enzyme Biosensors, Analytica Chimica Acta, 1995, pp. 275-283, vol. 303, No. 2-3, Elservier Science B.V.

I.M. Kolthoff, Voltammetric Determination of Ultratraces of Albumin, Cysteine, and Cystine at the Hanging Mercury Drop Electrode, Analytical Chemistry, 1977, pp. 2108-2109, vol. 49, No. 13.

E. Csoregi, et al., Carbon Fibres as Electrode Materials for the Construction of Peroxidase-Modified Amperometric Biosensors, Analytica Chimica Acta, 1993, pp. 59-70, vol. 273, No. 1/2, Elservier Science B.V.

G. Cui, et al., Effect of Pre-Treatment on the Surface and Electrochemical Properties of Screen-Printed Carbon Paste Electrodes, The Analyst, 2001, pp. 1399-1403, vol. 126.

International Search Report and Written Opinion corresponding to PCT/GB2005/002551, under date of mailing of Jan. 5, 2006.

* cited by examiner

ELECTRODE PRECONDITIONING

This application is a §371 National Stage Entry of PCT/GB2005/002551 filed on Jun. 29, 2005.

FIELD OF THE INVENTION

The present invention relates to an electrochemical sensing method and an electrochemical sensing device.

BACKGROUND TO THE INVENTION

A number of electrochemical sensing techniques for detecting the presence of a metal ion in a sample are dependant on the adsorption of the metal ion on a working electrode. In such techniques, typically the oxidation or reduction of the metal ion can only take place when the metal ion is adsorbed on the electrode. However, many metal ions do not adsorb efficiently on electrode surfaces, in particular carbon surfaces. Electrochemical sensing of the presence of such metal ions can therefore be unreliable, especially where the metal ion is present in the sample only in small amounts. Particular difficulties are experienced when the adsorption of the metal ion on the electrode is in competition with binding to another substance in the sample to be tested.

A new technique is therefore required which addresses the difficulties of poor adsorption of metal ions on electrodes.

SUMMARY OF THE INVENTION

The present invention therefore provides an electrochemical sensing method comprising
(a) providing an electrochemical cell having a working electrode and a pseudo reference electrode;
(b) providing a sample comprising a metal, the sample being in contact with the working electrode and the metal being capable of being oxidised or reduced at the working electrode when the metal is adsorbed on the working electrode;
(c) preconditioning the working electrode by (i) applying a time varying preconditioning potential between the working and pseudo reference electrodes; and/or (ii) baking the working electrode; and/or (iii) air-ageing the working electrode; and subsequently
(d) applying a measuring potential between the working and pseudo reference electrodes and, during application of said measuring potential, measuring the current generated by oxidation/reduction of the metal at the working electrode,
wherein steps (a), (b), (ci), (cii) and (ciii) may be carried out in any order and step (d) is carried out after steps (a), (b) and (c).

The present inventors have found that preconditioning the working electrode prior to measurement may increase the degree of adsorption of the metal (which may be a metal ion) on the working electrode, and accordingly increases the definition of the measured metal oxidation/reduction peak. It is thought that the preconditioning step may cause removal of contaminants from the electrode surface and may additionally alter the surface of the electrode so that it is more active. Improvements in the oxidation/reduction peak are observed when any one or more of preconditioning methods (i) to (iii) are applied. Similar effects are not observed, however, when a potentiostatic preconditioning potential is applied.

The increased definition of the oxidation/reduction peak observed enables more accurate electrochemical detection, in particular when the amount of metal to be detected is small.

The present invention also provides a device comprising
an electrochemical cell having a working electrode and a pseudo reference electrode;
a potentiostat for applying a potential between the working and pseudo reference electrodes;
a controller for controlling the potentiostat so that firstly a time varying preconditioning potential is applied and subsequently a measuring potential is applied; and
means for measuring the current across the cell.

In an alternative embodiment, the invention provides a device comprising
an electrochemical cell having a working electrode and a pseudo reference electrode;
a potentiostat for applying a potential between the working and pseudo reference electrodes;
a controller for controlling the potentiostat; and
means for measuring the current across the cell;
wherein the working electrode is a preconditioned electrode obtained by subjecting the electrode to baking or air-ageing.

DETAILED DESCRIPTION OF THE INVENTION

Figure 1:
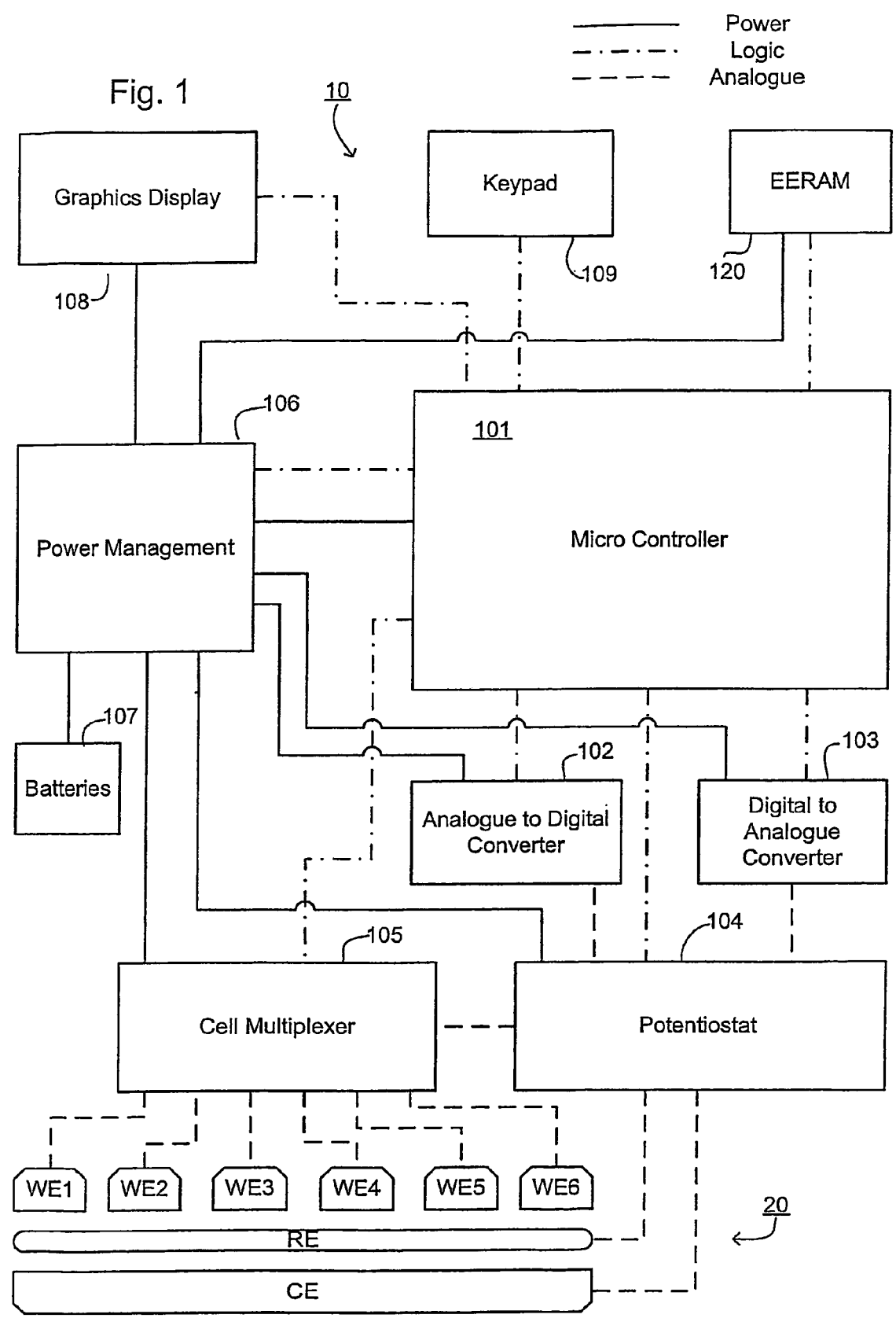
FIG. 1 is a schematic drawing of a portable electrochemical sensor device incorporating the invention.
Figure 2:
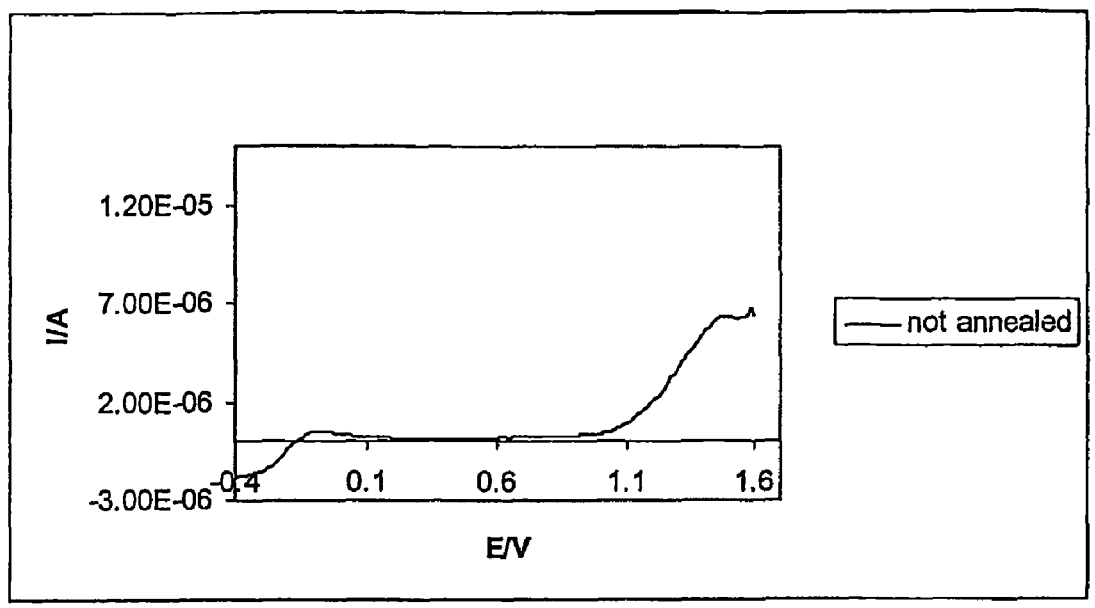
FIGS. 2, 3, 4, and 5 each show a plot of current (A) versus potential (V) obtained by carrying out an electrochemical measurement on a device in which the working electrode has been baked for (i) 0 hours (FIG. 2); (ii) 2 hours (FIG. 3); (iii) 4 hours (FIG. 4); and (iv) 21.5 hours (FIG. 5)
Figure 3:
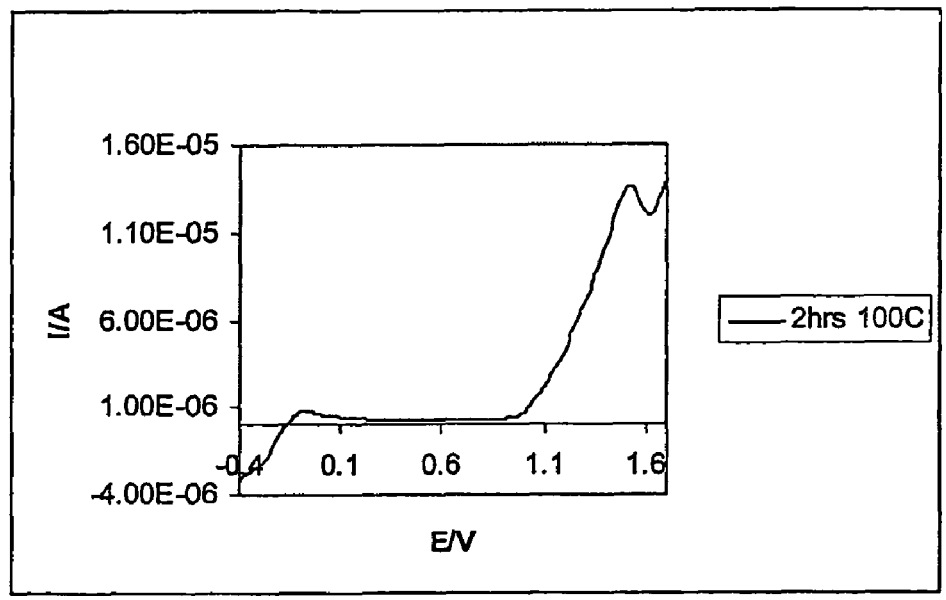
Figure 4:
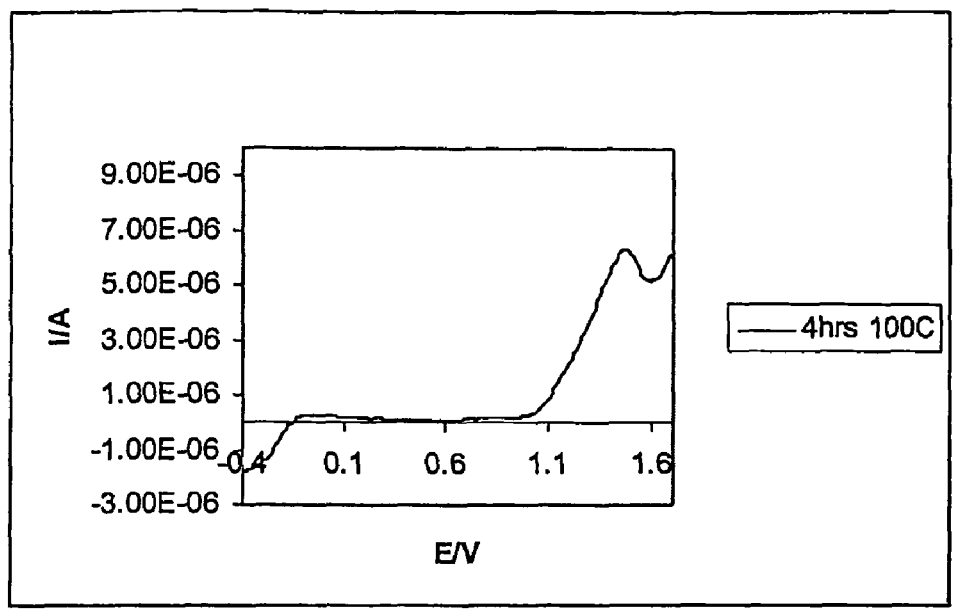
Figure 5:
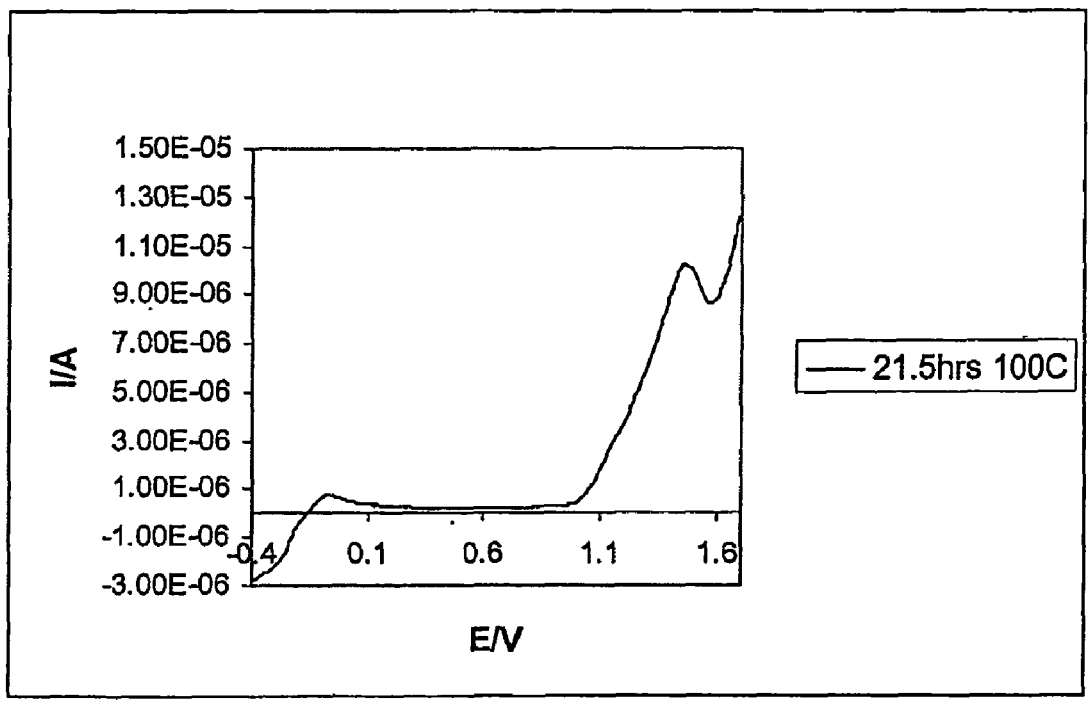

The method of the present invention involves preconditioning the working electrode by (i) applying a time varying preconditioning potential between the working and counter electrodes; and/or (ii) baking the working electrode; and/or (iii) air-ageing the working electrode. One or more of the preconditioning methods (i) to (iii) may be used, for example a pre-conditioning potential may be used alone, or application of a preconditioning potential may be combined with baking or air-ageing.

The pre-conditioning step (c) may be carried out before or after steps (a) and/or (b). If two or more pre-conditioning methods are used, these are carried out either simultaneously or separately. Where, for example, a preconditioning potential is used in combination with baking or air-ageing, the baking or air-ageing step is typically carried out before step (b) and the preconditioning potential applied after step (b). The preconditioning step is completed prior to application of the measuring potential in step (d).

In one embodiment, the method of the invention involves preconditioning the working electrode by applying a time varying preconditioning potential across the cell prior to application of the measuring potential. The current generated by the cell is measured during application of the measuring potential. Typically, the preconditioning potential is applied after provision of a sample to the electrochemical cell in step (b).

Typically, the time varying preconditioning potential is applied by varying the potential between a first (lower) applied potential of no more than −0.5V and a second (upper) applied potential of at least 1.1V. The first applied potential is preferably no more than −0.4V. The second applied potential is preferably at least 1.2V, for example at least 1.4V, 1.5V or 1.7V. These voltages are each quoted against a Ag/AgCl reference electrode.

As used herein, "no more than" −0.4V means a potential of −0.4V or a less negative potential. Similarly, "no more than" −0.5V means a potential of −0.5V or a less negative potential.

As used herein, all voltages are quoted in accordance with the IUPAC convention.

In one embodiment of the invention, the preconditioning is carried out by scanning the applied potential by decreasing the applied potential from substantially zero to said first applied potential and then increasing the applied potential to said second applied potential. The applied potential is then typically brought to substantially zero before applying the measuring potential. The preconditioning scan is typically carried out either once or twice before the measuring potential is applied. The measuring potential may be applied immediately after the preconditioning potential, or there may be a time lapse between the preconditioning and measuring potentials.

The rate of varying the potential during the preconditioning scan is typically from 1 $mVs^{-1}$ to 2 $Vs^{-1}$, more preferably from 10 $mVs^{-1}$ to 1.5 $Vs^{-1}$, for example from 50 $mVs^{-1}$ to 1 $Vs^{-1}$.

In a further embodiment, the preconditioning step comprises baking the working electrode. This is typically achieved by placing a device comprising the working electrode in an oven and heating at a temperature of from 70 to 130° C. preferably from 90 to 110° C. Baking is typically carried out for from 1 hr to 20 hrs preferably up to 10 hrs, more preferably from 1 to 5, for example from 2 to 3 hours. Baking is preferably carried out in air. Typically, baking is carried out for approximately 3 hours at about 100° C.

In a further embodiment, the preconditioning step comprises air-ageing the working electrode. This is typically achieved by exposing the working electrode to air for from 10 to 20 days, preferably 12 to 18 days, for example about 14 days. Air-ageing is typically carried out at room temperature, for example from 18 to 25° C. Both air-ageing and baking are typically carried out prior to the provision of a sample in step (b).

It is thought that the use of a preconditioning step may alter the surface of the electrode making it more favourable for adsorption of metals. In the case of a carbon working electrode, one possible theory is that each preconditioning method (i) to (iii) causes carboxyl groups to form on the surface of the electrode. The presence of carboxyl groups encourages certain metals to adsorb. In the case of the preconditioning potential, water may be oxidised/reduced at the surface of the electrode during application of the preconditioning potential, causing OH radicals to form in the vicinity of the working electrode. The OH radicals may react with the carbon on the electrode surface forming carboxyl groups. It is to be understood, however, that the present invention is not bound by this theory.

The measuring potential can be applied in any way which is suitable for the metal to be detected. The measuring potential may therefore be either time varying or static. For example, when the metal to be detected is cobalt, the measuring potential is typically time varying, the potential being varied at a slower rate than the preconditioning potential (if used), for example at a rate of about 50 $mVs^{-1}$. Application of the measuring potential may, for example, comprise increasing the applied potential to at least 1.4V, preferably at least 1.6V, more preferably at least 1.8V, 1.9V or 2.0V. In one embodiment of the invention, application of the measuring potential comprises scanning the potential between first and second applied potentials as described above with reference to the preconditioning potential, although typically using a slower scanning rate.

The sample which is provided in the method of the invention is in a form which enables electrical contact to occur between the metal contained in the sample and the working electrode. Typically, the sample is a fluid (e.g. a liquid) or a gel. For example, the sample may be a sample of bodily fluid from a patient, e.g. blood or plasma.

The method of the present invention is useful for the electrochemical sensing of any metal whose oxidation/reduction relies on the adsorption of the metal to the working electrode. In the context of the present invention "metal" means a metal in any oxidation state which is capable of being oxidised or reduced at the working electrode when the metal is adsorbed to the working electrode. The metal may, for example, be a metal ion, or a metal contained in a metal complex. Typically, the metal is a metal ion. Typically, substantially no oxidation or reduction of the metal occurs on application of a potential to an electrochemical cell in which a sample comprising the metal is in contact with the working electrode but in which the metal is not adsorbed to the working electrode.

When a metal is said to be adsorbed to the working electrode, this encompasses both physical and chemical adsorption. Typically, when the metal is absorbed to the electrode, a measurable increase in current due to oxidation or reduction of the metal is observed compared with the situation in which the metal is not adsorbed to the electrode.

The method of the present invention is particularly suitable for use in the electrochemical detection of cobalt. Cobalt (II) is oxidised at the working electrode on application of a potential of approximately 1.4V or more (voltage quoted against an Ag/AgCl reference electrode). However, a significant degree of oxidation will only occur if the cobalt is adsorbed on the surface of the electrode. The use of a preconditioning step in accordance with the present invention has been found to significantly increase the definition of the cobalt oxidation peak observed, when compared with measurements carried out without use of a preconditioning step. This is believed to be due to increased adsorption of cobalt on the electrode.

In particular, the present invention is useful in methods for the electrochemical diagnosis of ischemia and related methods, for example the methods described in British Patent Application GB 0414551.2 and the international application claiming priority therefrom (filed on the same day as the present application and entitled "ELECTROCHEMICAL SENSOR"), which correspond to U.S. Published Patent Application No. 2009/294304, the contents of which are incorporated herein by reference in their entirety.

The method of the present invention may be carried out on any device comprising an electrochemical cell. The working electrode of the electrochemical cell is, for example, formed of carbon, gold, palladium or platinum, preferably carbon. The electrochemical cell may be either a two-electrode or a three-electrode system. A two-electrode system comprises a working electrode and a pseudo reference electrode. A three-electrode system comprises a working electrode, a pseudo reference electrode and a separate counter electrode. As used herein, a pseudo reference electrode is an electrode that is capable of providing a reference potential. In a two-electrode system, the pseudo reference electrode also acts as the counter electrode and is thus able to pass a current without substantially perturbing the reference potential.

Exemplary devices which can be employed in the method of the present invention include those described in PCT International patent Application WO 03/056319 which corresponds to U.S. Published Patent Application 2005/178674. Further suitable devices are those described in British Patent Application GB 0414546.2 and the international application claiming priority therefrom (filed on the same day as the present application and entitled ELECTRODE FOR ELECTROCHEMICAL SENSOR) corresponding to U.S. Published Patent Application 2008/190783. These documents are incorporated herein in by reference in their entirety.

One embodiment of the present invention is depicted in FIG. 1. In this embodiment, the sensor device comprises an electronics unit 10 to which is connected an electrode unit 20, which may be disposable. The electrode unit 20 has a plurality of working electrodes WE1-WE6 as well as reference and counter (auxiliary) electrodes RE, CE. In some embodiments of the invention, the reference and counter electrodes may be combined. Different working electrodes WE1-WE6 may be adapted to select different ions for measurement, as described in WO 03/012417 (which is incorporated herein by reference in its entirety) and WO 03/056319, referenced above.

An electrochemical cell is formed between the working and counter electrodes. To make measurements of a fluid that is in electrical connection with a working electrode, a measuring potential is applied between the working electrode and a reference/counter electrode and the resulting current detected. The same or different measuring potentials can be applied between a reference/counter electrode and each different working electrode.

Overall control of the electronics unit 10 of the sensor device is performed by a micro controller 101 which controls a potentiostat 104 via digital to analog converter 103 and receives measurement results from the potentiostat 102 via analog to digital converter 102. The potentiostat 104 applies the desired voltages to the working, reference and counter electrodes WE, RE, CE; a cell multiplexor 105 under the control of microprocessor 101 selects the appropriate one of the working electrodes.

A graphics display 108 enables display of operating menus to the user, options being input via keypad 109, and measurement results. An electrically erasable RAM 120 allows for storage of both system software and measurement results. A bar code reader may also be provided for input of data, especially of patient information if the sensor is used in a medical or veterinary application. Interfaces, e.g. conforming to RS232, Bluetooth, Ethernet, USB, or WiFi (IEEE 802.11a, b, etc.) standards, may be provided for connection to printers, networks and other devices, e.g. patients records systems.

Power is supplied from batteries 107 under the control of a power management unit 106 that optimises battery life and controls recharging of the batteries.

EXAMPLES

Example 1

Electrochemical tests were carried out using devices of the type described in British Patent Application GB 0414546.2 and the international application claiming priority therefrom (filed on the same day as the present application and entitled ELECTRODE FOR ELECTROCHEMICAL SENSOR) that correspond to U.S. Published Patent Application 2008/190783. The working electrode of the electrochemical cells was a carbon electrode and a Ag/AgCl pseudo reference electrode acting as both counter and reference electrodes was used.

A first device (i) was not annealed (baked). Three further devices were annealed at a temperature of 100° C. for (ii) 2 hours, (iii) 4 hours and (iv) 21.5 hours in order to precondition the working electrode.

A reagent mixture comprising cobalt (II) chloride was inserted into each device and dried into position. Plasma was provided to each electrochemical cell and the dried reagent mixture allowed to re-suspend in the plasma. The plasma comprising suspended reagent mixture was in contact with the working electrode of the electrochemical cell.

A preconditioning scan was applied at a scan rate of 100 $mVs^{-1}$, the applied potential being first decreased to approximately −0.4V and subsequently increased to approximately 1.7V. A measuring scan was then applied over the same voltage range but using a scan rate of 50 $mVs^{-1}$. The current was measured during application of the measuring scan.

FIGS. 2 to 5 depict the measured current for cells (i) to (iv) respectively. The cobalt (II) oxidation peak appears at approximately 1.5V. As is shown by the Figures, the definition of the cobalt oxidation peak improves with increased annealing time.

Example 2

Figure 6:
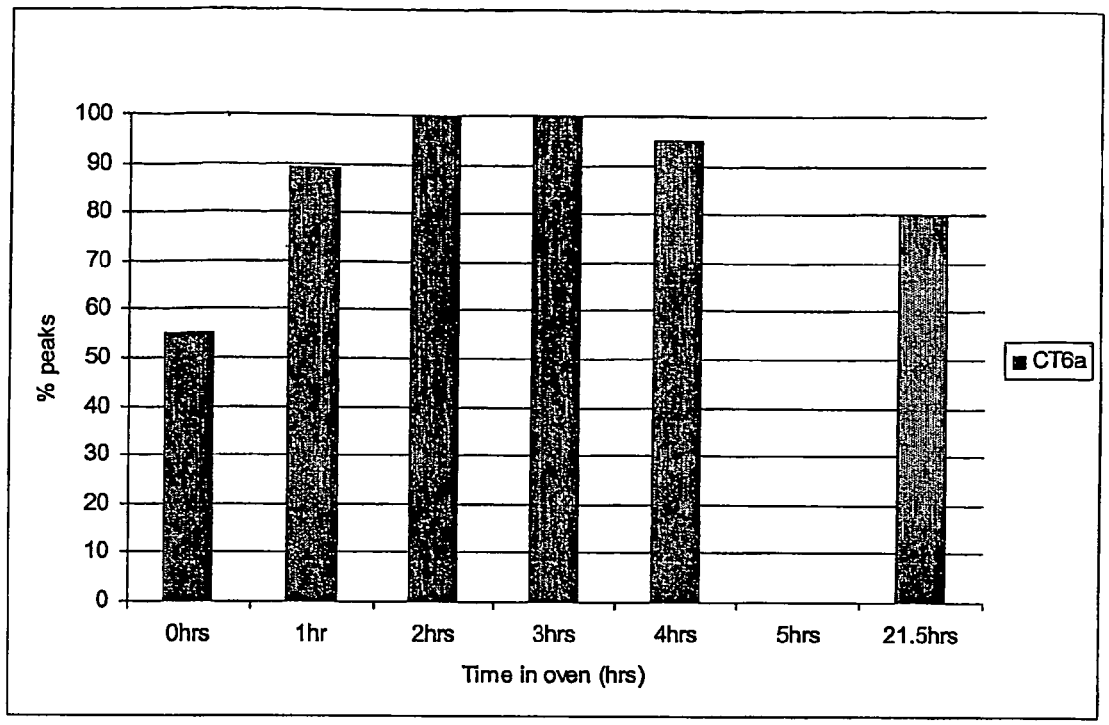
FIG. 6 depicts a plot of the percentage of cobalt oxidation peaks which are well-defined and measurable by a peak detection algorithm for preconditioning methods involving baking the working electrode for varying times.

Example 1 was repeated, but applying different annealing times to a number of different devices. Annealing times of 0 hrs, 1 hr, 2 hrs, 3 hrs, 4 hrs and 21.5 hrs were applied to groups of 20 electrochemical cells. For each annealing time, the percentage of cobalt oxidation peaks detectable using a peak detection algorithm was determined. FIG. 6 records the percentage of detectable peaks for each annealing time, showing a maximum at annealing times of 2 and 3 hours. This demonstrates an improvement in cobalt (II) oxidation peak definition at these annealing times.

Example 3

Example 1 was repeated on a number of devices, but without annealing the electrodes. The devices used were manufactured in two separate batches (I12 and I14). In this Example, prior to addition of the reagent mixture, the devices were stored in the dark at temperatures of between 19 and 24° C. to air-age the electrodes for varying periods of time. The storage periods used ranged from 0 to 14 days. The storage period starts from the time at which the working electrode surface is defined. In the case of the devices of British Patent Application GB 0414546.2 and the international application claiming priority therefrom (filed on the same day as the present application and entitled ELECTRODE FOR ELECTROCHEMICAL SENSOR) that correspond to U.S. Published Patent Application 2008/190783, which were used in this Example, the starting point is the time at which a hole is punched to form the receptacle of the cell, as well as the working electrode. The air-ageing time is therefore defined as the time from punching to reaction.

Figure 7:
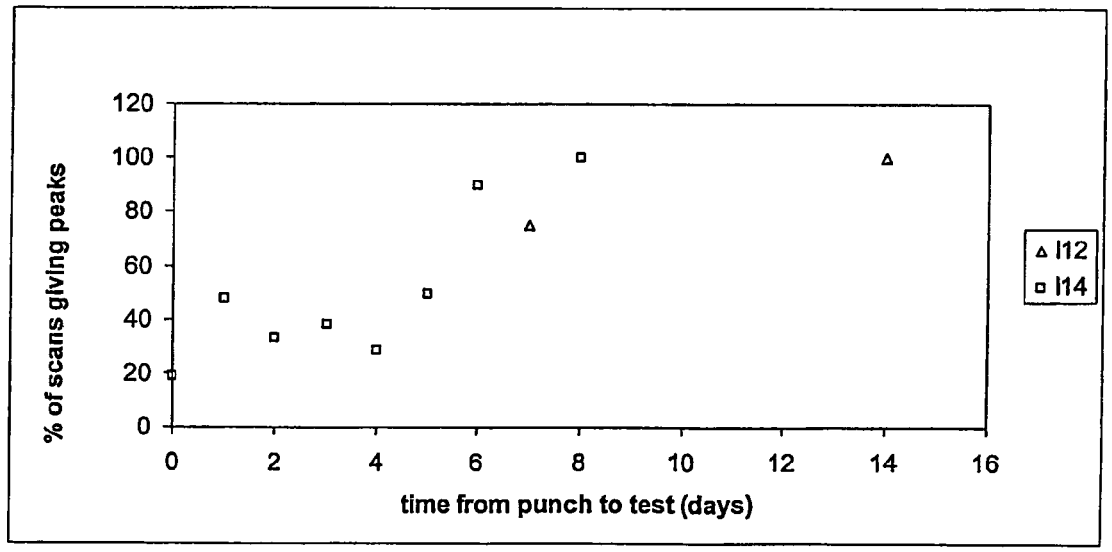
FIG. 7 depicts a plot of the percentage of cobalt oxidation peaks which are well-defined and measurable by a peak detection algorithm for preconditioning methods involving air-ageing the working electrode for varying times.

For each air-ageing time, the percentage of cobalt oxidation peaks detectable using a peak algorithm was determined FIG. 7 records the percentage of detectable peaks for each air-ageing time, showing a gradual increase in detectable peaks as the air-ageing time increases, with a maximum being reached at about 8-10 days. This demonstrates an improvement in cobalt (II) oxidation peak definition with increasing air-ageing preconditioning.

Example 4

Figure 8:
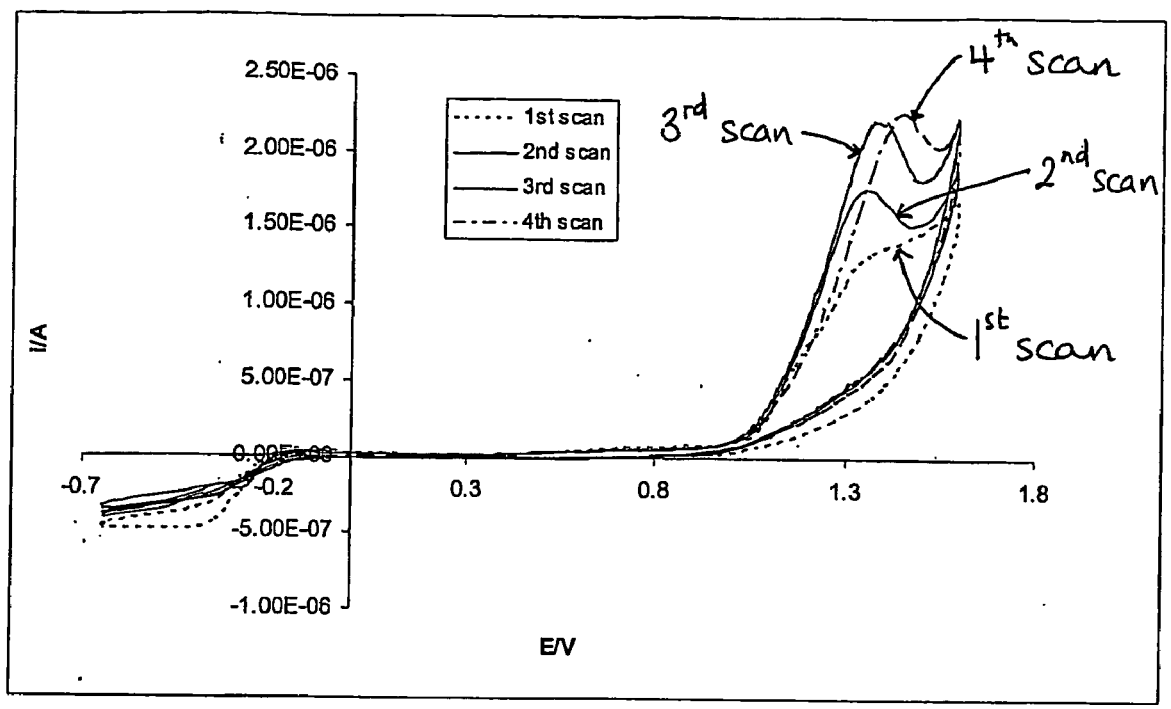
FIG. 8 depicts a plot of current (A) versus potential (V) for four electrochemical cells wherein a preconditioning scan was carried out 1, 2, 3 or 4 times.

Example 1 was repeated, with the exception that annealing was not carried out. Further, instead of the preconditioning and measuring scans described in Example 1, the potential was scanned four times, each at a rate of 50 mVs$^{-1}$, the scan ranging from −0.4V to 1.7V. The current was measured during each scan and the measured currents for the $1^{st}$, $2^{nd}$, $3^{rd}$ and $4^{th}$ scans are recorded in FIG. 8. The definition of the cobalt oxidation peak at 1.4V for the first scan (i.e. no preconditioning scan) is poor. In contrast, the peak definition is significantly improved for the $2^{nd}$, $3^{rd}$ and $4^{th}$ scans (where in effect 1, 2 and 3 preconditioning scans are carried out).

Whilst the invention has been described above in relation to a specific embodiment and Examples, the present invention may be embodied in other forms. The scope of the invention is therefore determined by the appended claims rather than the foregoing description.

The invention claimed is:

1. A device comprising
   an electrochemical cell having a working electrode and a pseudo reference electrode;
   an electroactive substance capable of undergoing an electrochemical reaction when in contact with a sample of bodily fluid, the electroactive substance comprising an electrocatalyst and a mediator;
   a potentiostat for applying a potential between the working and pseudo reference electrodes;
   a controller programmed to operate the potentiostat to apply firstly a time varying preconditioning potential between the working and pseudo reference electrodes consisting of carrying out at least one but no more than two preconditioning scans, and subsequently to apply a measuring potential between the working and pseudo reference electrodes, wherein in the or each preconditioning scan the applied potential is decreased from substantially 0 to a first applied potential of no more than −0.5V and then increased to a second applied potential of at least 1.1V; and
   means for measuring the current across the cell, wherein said means is configured to measure the current during application of the measuring potential.

2. A device according to claim 1, which additionally comprises a composition comprising a metal which is capable of being oxidised or reduced at the working electrode when the metal is adsorbed on the working electrode.

3. A device according to claim 1, wherein the controller is programmed to operate the potentiostat to apply a time varying preconditioning potential by carrying out a preconditioning scan of the applied potential comprising decreasing the applied potential from substantially zero to said first applied potential and then increasing the applied potential to said second applied potential.

4. A device according to claim 3 wherein the controller is programmed to operate the potentiostat to carry out two said preconditioning scans of the applied potential.

5. A device according to claim 3 wherein the controller is programmed to operate the potentiostat such that the rate of varying the potential during the said one or two preconditioning scans is from 1 mVs$^{-1}$ to 2 Vs$^{-1}$.

6. A device according to claim 3 wherein the controller is programmed to operate the potentiostat such that after the said one or two preconditioning scans the applied potential is brought to substantially zero before applying the measuring potential.

* * * * *

UNITED STATES PATENT AND TRADEMARK OFFICE
CERTIFICATE OF CORRECTION

PATENT NO. : 8,282,797 B2  
APPLICATION NO. : 11/630494  
DATED : October 9, 2012  
INVENTOR(S) : Hyland et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 697 days.

Signed and Sealed this  
Tenth Day of June, 2014

Michelle K. Lee  
*Deputy Director of the United States Patent and Trademark Office*